United States Patent
Lehnen et al.

(10) Patent No.: US 6,404,912 B1
(45) Date of Patent: *Jun. 11, 2002

(54) METHOD AND APPARATUS FOR VISUALLY INSPECTING AN OBJECT

(75) Inventors: David Charles Lehnen; Christopher John LeBeau, both of Tempe; Tonya Marie Twine, Phoenix, all of AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/631,751

(22) Filed: Aug. 4, 2000

Related U.S. Application Data

(63) Continuation of application No. 09/087,884, filed on Jun. 1, 1998, now Pat. No. 6,160,906.

(51) Int. Cl.[7] ................................................. G06K 9/00
(52) U.S. Cl. ........................ 382/151; 348/87; 382/152
(58) Field of Search ............................... 382/141, 145, 382/151, 152, 144, 149, 150; 348/126, 131, 86, 87, 125

(56) References Cited

U.S. PATENT DOCUMENTS

| | | | |
|---|---|---|---|
| 4,750,035 A | 6/1988 | Chang et al. | 358/106 |
| 5,214,841 A | 6/1993 | Howard et al. | 29/721 |
| 5,402,505 A | 3/1995 | Roy et al. | 382/8 |
| 5,519,513 A | 5/1996 | Copenhaver et al. | 358/475 |
| 5,617,209 A | 4/1997 | Svetkoff et al. | 356/376 |
| 5,699,447 A | 12/1997 | Alumot et al. | 382/145 |
| 6,160,906 A | * 12/2000 | Lehnen et al. | 382/145 |

* cited by examiner

Primary Examiner—Bhavesh Mehta
(74) Attorney, Agent, or Firm—Anthony M. Martinez; Mark J. Fink

(57) ABSTRACT

A pickup tool (30) has reflective surfaces (42, 44, 46, 48) attached thereto. The pickup tool (30) picks up an object (38) and moves the object (38) over a light source (51). The reflective surfaces (42, 44, 46, 48) reflect a light beam (61) emitted from the light source (51), generating deflected light beams (63, 65, 67, 69) which back light the object (38). The deflected light beams (63, 65, 67, 69) form silhouette images of the object (38) in cameras (52, 54, 56, 58). A visual inspection of the object (38) is performed by analyzing the images.

8 Claims, 3 Drawing Sheets

METHOD AND APPARATUS FOR VISUALLY INSPECTING AN OBJECT

The present application is a continuation of prior U.S. application Ser. No. 09/087,884, filed on Jun. 1, 1998, now U.S. Pat. No. 6,160,906, which is hereby incorporated by reference, and priority thereto for common subject matter is hereby claimed.

BACKGROUND OF THE INVENTION

The present invention relates, in general, to visual inspection of an object and, more particularly, to an apparatus and a process for visually inspecting an object.

Typically, work pieces such as semiconductor devices are visually inspected to insure that they meet design specifications for parameters such as lead coplanarity, lead length, lead straightness, mark inspection, surface inspection, lead pitch, etc. The visual inspection of a semiconductor device is conventionally performed using a visual inspection station. The semiconductor device is placed on the visual inspection station. Using either a front lighting technique or a back lighting technique, the images of the semiconductor device are formed and analyzed using a vision computer. If the semiconductor device meets predetermined design specifications, the device passes the inspection and is moved to the next stage of the manufacturing process. Otherwise, the device is rejected. The conventional visual inspection process disrupts the process of handling the semiconductor device and is often time consuming. Further, it is difficult to incorporate the conventional visual inspection process in an automated device handling process that is both cost efficient and time efficient.

Accordingly, it would be advantageous to have an apparatus and a method for visually inspecting an object in an automated process of handling the object. It is desirable for the method to be simple and time efficient. It is also desirable for the apparatus to be inexpensive. It would be of further advantage for the apparatus to be compatible with existing object handling equipment and process.

Figure 1:
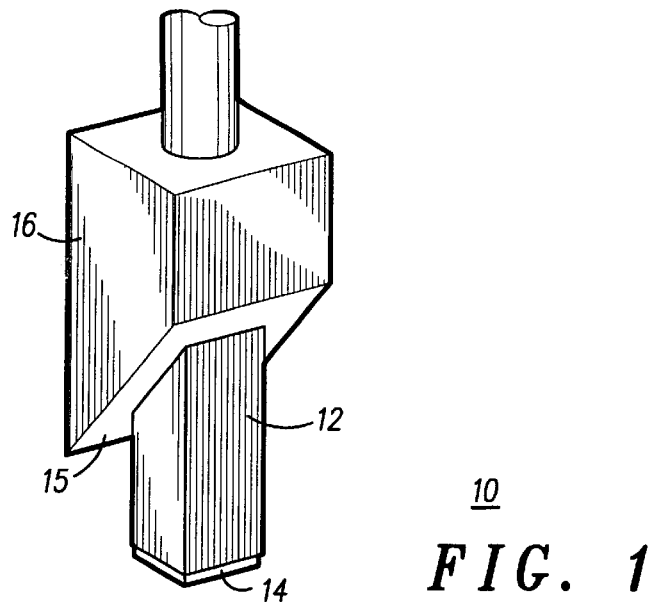
FIG. 1 is an isometric view of an apparatus that can be used for visually inspecting an object in accordance with a first embodiment of the present invention.

It should be understood that for simplicity and clarity of illustration, the figures are not necessarily drawn to scale. It should also be understood that, where considered appropriate, reference numerals have been repeated among the figures to indicate corresponding or analogous elements.

DETAILED DESCRIPTION OF THE DRAWINGS

Generally, the present invention provides an apparatus and a method for visually inspecting an object in an automated object handling process. In accordance with the present invention, the object is picked up by a pickup tool. A light source illuminates a portion of the pickup tool adjacent the object when the pickup tool is at a predetermined position relative to the light source. In accordance with one embodiment, a deflector on the pickup tool reflects a portion of a incident light beam from the light source to generate a deflected light beam. The deflected light beam back lights the object in a first direction and forms a first silhouette of the object. Another portion of the incident light beam back lights the object in a second direction and forms a second silhouette of the object. The first and second silhouette images of the object have different directions of views. In accordance with another embodiment, several deflectors attached to the pickup tool reflect different portions of the incident light beam to generate several deflected light beams in different directions. These deflected light beams back light different portions of the object and generate silhouettes thereof. In both embodiments, the location and orientation of a reflective surface relative to the pickup tool are fixed and can be accurately determined. Thus, the pickup tool can serve as a reference frame when the images of the object are reconstructed in a vision computer and the geometrical properties of the object are examined. Therefore, the visual inspection can be performed while the pickup tool picks up the object and moves it from one place to another place. More particularly, the object does not need to be placed on an inspection station for visual inspection.

FIG. 1 illustrates, in an isometric view, an inspection apparatus 10 in accordance with a first embodiment of the present invention. Apparatus 10 includes a pole 12. At one end of pole 12, there is an object pickup mechanism 14. By way of example, pickup mechanism 14 is a vacuum mechanism. A shaft 16 surrounds a portion of pole 12. Pole 12 and shaft 16 can be made of metal, plastic, etc. Pole 12 and shaft 16 can be made as an integral part or as two parts attached to each other. Shaft 16 has an inclined end surface at a distance from the end of pole 12. There is a reflective surface 15 formed on the inclined end surface of shaft 16. Reflective surface 15 functions as a deflector to deflect light. In one embodiment, shaft 16 is a metal shaft and the inclined end surface of shaft 16 is a polished metal surface, serving as inclined reflective surface 15. In another embodiment, inclined reflective surface 15 is formed by attaching a mirror to the inclined end surface of shaft 16. By way of example, a normal line (not shown) of inclined reflective surface 15 makes an angle of approximately 45 degrees (°) with respect to a direction parallel to pole 12 (the vertical direction in FIG. 1). Preferably, the geometrical parameters of apparatus 10 such as, for example, the position and orientation of inclined reflective surface 15 with respect to pickup mechanism 14 at the end of pole 12 are determined to a high degree of accuracy. Accordingly, when apparatus 10 picks up an object in a visual inspection process, the position and orientation of the object with respect to apparatus 10 can be accurately measured using a feature, e.g., the boundary of reflective surface 15, as a reference position.

The function of apparatus 10 is picking up an object such as, for example, a semiconductor device and transporting the object from one location to another location. In the process of transporting the object, a visual inspection of the object is performed. Therefore, apparatus 10 is also referred to as a visual inspection tool or a pickup tool. It should be understood that FIG. 1 only shows a portion of apparatus 10 that is related to the visual inspection of the object. Apparatus 10 also includes an operating system (not shown), e.g., an electric-mechanic system, a hydraulic system, a pneumatic system, or the like, for picking up, transporting, and releasing the object. It should also be understood that the structure of apparatus 10 is not limited to being that described hereinbefore and shown in FIG. 1. For example, pickup mechanism 14 is not limited to being a vacuum mechanism. Any mechanism, e.g., a clasp mechanism, a latch mechanism, a magnetic mechanism, etc., capable of picking up the object to be inspected can be used as pickup mechanism 14 in apparatus 10. Pole 12 and shaft 16 are not limited to having rectangular cross sections as shown in FIG. 1. The cross sections of pole 12 and shaft 16 can have any shape, e.g., circular, elliptical, triangular, pentagonal, hexagonal, etc. Further, shaft 16 is optional in apparatus 10. In an alternative embodiment (not shown) of the present invention, apparatus 10 does not include shaft 16 and inclined reflective surface 15 is formed by mounting or attaching a reflective plane, e.g., a mirror, directly to pole 12. In addition, apparatus 10 can include one or more reference marks (not shown) on inclined reflective surface 15. The reference marks facilitate the accurate measurement of the position and orientation of the object with respect to apparatus 10.

Figure 2:
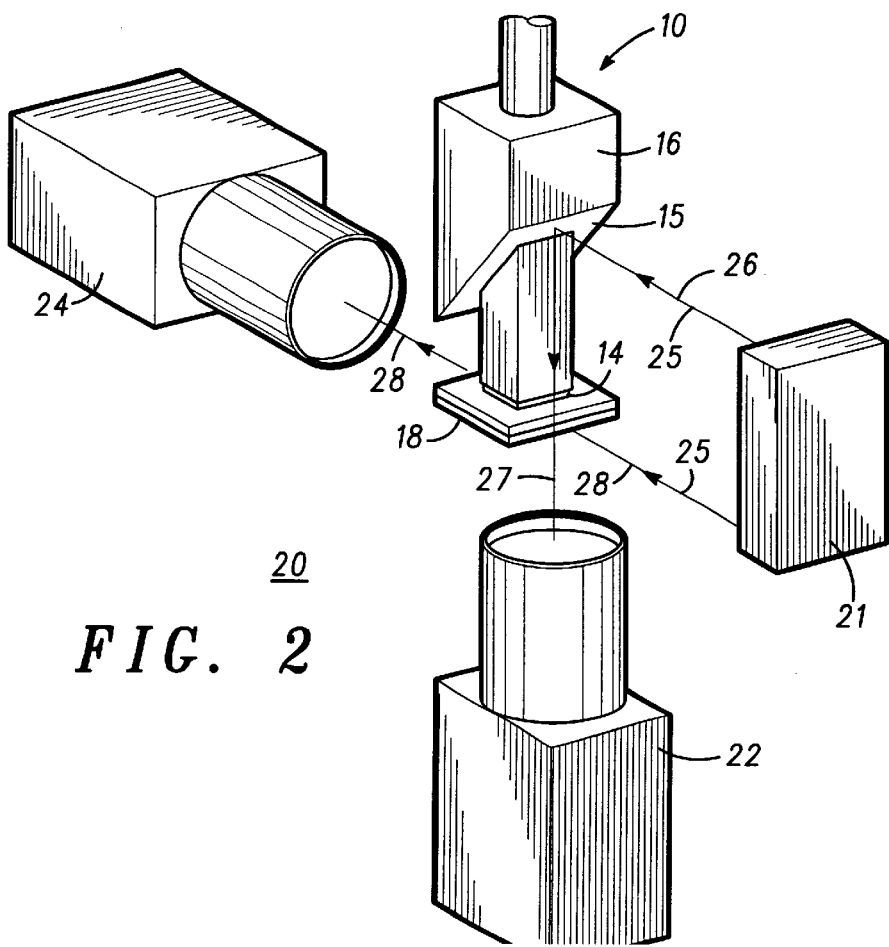
FIG. 2 schematically illustrates a system that uses the apparatus of FIG. 1 for visually inspecting an object in accordance with the first embodiment of the present invention.

FIG. 2 schematically illustrates a system 20 that includes apparatus 10 of FIG. 1 and is used for visually inspecting an object 18 in accordance with the first embodiment of the present invention. System 20 is also referred to as an optical system or an inspection system. By way of example, object 18 is a semiconductor device. Apparatus 10 picks up semiconductor device 18 from one location and transports it to another location during a semiconductor device packaging process. Inspection system 20 also includes a light source 21 and cameras 22 and 24. In one embodiment, light source 21 is a light source, e.g., a light emitting diode, that emits a continuous light. In the process of transporting semiconductor device 18, apparatus 10 stops at a position relative to light source 21 and cameras 22 and 24 as shown in FIG. 2 for a short time interval, e.g., 0.25 second. Cameras 22 and 24 record the silhouette images of semiconductor device 18 during this time interval. In another embodiment, light source 21 is a strobe light source and emits a strobe light when apparatus 10 moves into the position shown in FIG. 2. Cameras 22 and 24 record the silhouette images of semiconductor device 18 formed by the strobe light. A vision computer (not shown) coupled to cameras 22 and 24 analyzes the images and examines the geometrical property of semiconductor device 18 and the position and orientation of semiconductor device 18 relative to apparatus 10.

In the visual inspection process, light source 21 emits a light beam 25 illuminating, at least partially, apparatus 10 and semiconductor device 18. By way of example, light beam 25 is a substantially collinear light beam that is substantially perpendicular to pole 12. A portion 26 of light beam 25 is reflected by inclined reflective surface 15, thereby generating a deflected light beam 27 substantially parallel to pole 12. Deflected light beam 27 back lights semiconductor device 18 and forms a silhouette image thereof in camera 22. A portion 28 of light beam 25 illuminates semiconductor device 18 directly and forms a silhouette image thereof in camera 24. The silhouette image of semiconductor device 18 formed by deflected light beam 27 has a direction of view different from that of the silhouette image formed by portion 28 of light beam 25. As shown in FIG. 2, deflected light beam 27 provides a top view of semiconductor device 18 and portion 28 of light beam 25 provides a side view of semiconductor device 18. The vision computer (not shown) coupled to cameras 22 and 24 analyzes the two images and inspect semiconductor device 18 for parameters such as, for example, lead coplanarity, lead length, lead straightness, mark inspection, surface inspection, lead pitch, etc. If they do not meet a predetermined design specification, semiconductor device 18 is rejected. After the visual inspection, a rejected device is transported to a predetermined location for disposal.

It should be noted that, when apparatus 10 picks up semiconductor device 18, there is usually a variation in the position and orientation of semiconductor device 18 with respect to apparatus 10. This variation will generally result in a variation in the position and orientation of semiconductor device 18 in its final location, which may present a problem in a packaging process that requires a high precision in the final position and orientation of semiconductor device 18. The visual inspection process of the present invention can solve that problem. In accordance with the present invention, the images in cameras 22 and 24 preferably also include the images of a portion of apparatus 10. Because the geometrical parameters of apparatus 10 such as, for example, the position and orientation of inclined reflective surface 15 with respect to pickup mechanism 14 are determined to a high degree of accuracy, analyzing the images provides accurate data about the position and orientation of semiconductor device 18 with respect to apparatus 10. These data are used in adjusting the position and orientation of apparatus 10 when apparatus 10 releases semiconductor device 18, thereby achieving precise position and orientation of semiconductor device 18 in its final location.

It should be understood that the structure and operation of inspection system 20 are not limited to being those described hereinbefore. For example, light source 21 can be a diffusive light source. In addition, inspection system 20 can include a deflector (not shown) and cameras 22 and 24 can be replaced with a single camera (not shown). The deflector can be made up of one or more lenses, one or more mirrors, or a combination of lenses and mirrors. The deflector deflects deflected light beam 27, portion 28 of light beam 25, or both after they pass semiconductor device 18 to generate two image light beams substantially parallel to each other. Therefore, the two silhouette images of semiconductor device 18 having different directions of views can be formed in the single camera.

Figure 3:
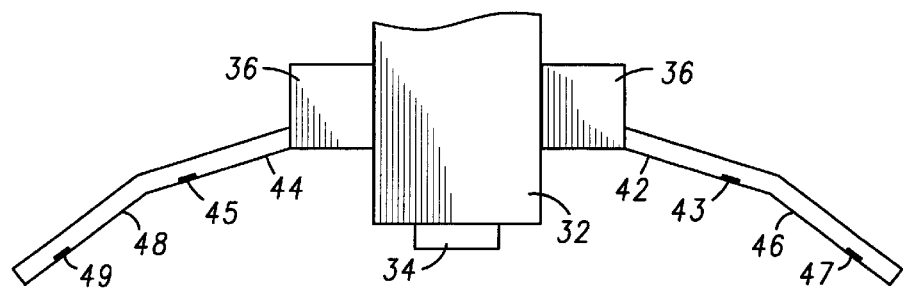
FIG. 3 is a cross-sectional view of an apparatus that can be used for visually inspecting an object in accordance with a second embodiment of the present invention.

FIG. 3 is a cross-sectional view of a visual inspection apparatus 30 in accordance with a second embodiment of the present invention. Apparatus 30 includes a pole 32. At an end of pole 32, there is an object pickup mechanism 34. By way of example, pickup mechanism 34 is a vacuum mechanism. Apparatus 30 functions to pick up an object such as, for example, a semiconductor device and transport the object from one location to another location. In the process of transporting the object, a visual inspection of the object is performed. Therefore, apparatus 30 is also referred to as a visual inspection tool or a pickup tool. A rectangular collar 36 surrounds a portion of pole 32. Pole 32 and collar 36 can be made of metal, plastic, etc. Collar 36 can be mounted to pole 32 or made as a part integral to pole 32. A reflective surface 42 and a reflective surface 44 are attached to opposite sides of collar 36. Each of normal lines (not shown) of reflective surfaces 42 and 44 makes an angle between approximately 5° and approximately 30° with respect to a direction substantially parallel to pole 32 (the vertical direction in FIG. 3). A preferred range of these two angles is between approximately 5° and approximately 27°. The values of these two angles depend on the size and shape of apparatus 30 and locations of cameras (shown in FIG. 4). In one embodiment, these two angles are approximately 17.5°.

Preferably, these two angles are approximately equal to each other. Therefore, reflective surfaces 42 and 44 form a substantially symmetric feature of apparatus 30 with respect to pole 32. A reflective surface 46 and a reflective surface 48 are attached to reflective surfaces 42 and 44, respectively. A normal line (not shown) of reflective surface 46 preferably makes an angle with respect to the direction parallel to pole 32 greater than the normal line of reflective surface 42. The difference between the two angles is between approximately 5° and approximately 30° and preferably at least 13°. Similarly, a normal line (not shown) of reflective surface 48 preferably makes an angle with respect to the direction parallel to pole 32 greater than the normal line of reflective surface 44. Preferably, reflective surfaces 46 and 48 are substantially symmetric with respect to pole 32. Therefore, the angle between the normal line of reflective surface 46 and the direction parallel to pole 32 and the angle between the normal line of reflective surface 48 and the direction parallel to pole 32 are preferably approximately equal to each other. By way of example, each of these two angles is between approximately 10° and approximately 45°. A preferred range of these two angles is between approximately 30° and approximately 42°. The values of these two angles depend on the geometry of apparatus 30 and locations of cameras (shown in FIG. 4). In one embodiment, these two angles are approximately 37.5°. Reflective surfaces 42, 44, 46, and 48 serve as deflectors and can be polished metal surfaces, mirrors, or the like. Further, apparatus 30 includes reference marks 43, 45, 47, and 49 on reflective surfaces 42, 44, 46, and 48, respectively. Preferably, the geometrical parameters of apparatus 30, e.g., the position and orientation of reflective surfaces 42, 44, 46, and 48 with respect to pickup mechanism 34 and the locations of reference marks 43, 45, 47, and 49 on corresponding reflective surfaces 42, 44, 46, and 48 are determined to a high degree of accuracy. Accordingly, when apparatus 30 picks up an object in a visual inspection process, the position and orientation of the object with respect to apparatus 30 can be accurately measured.

It should be understood that FIG. 3 only shows a portion of apparatus 30 that is related to the visual inspection of the object. Apparatus 30 also includes an operating system (not shown), e.g., an electric-mechanic system, a hydraulic system, a pneumatic system, or the like, for picking up, transporting, and releasing the object. It should also be understood that the structure of apparatus 30 is not limited to being that described hereinbefore. For example, pickup mechanism 34 is not limited to being a vacuum mechanism. Any mechanism, e.g., a clasp mechanism, a latch mechanism, a magnetic mechanism, etc., capable of picking up the object to be inspected can be used as pickup mechanism 34 in apparatus 30. In an alternative embodiment (not shown), apparatus 30 does not include collar 36 and reflective surfaces 42 and 44 are attached directly to pole 32. In addition, apparatus 30 is not limited to having four reference marks 43, 45, 47, and 49. Apparatus 30 can have any number of reference marks such as, for example, zero, one, two, three, five, six, seven, eight, etc. In an embodiment in which apparatus 30 does not have any reference mark, the position and orientation of the object relative to apparatus 30 can be determined using other features on apparatus 30, e.g., the corners of reflective surfaces 42, 44, 46, and 48, the line between reflective surfaces 42 and 46, the line between reflective surfaces 44 and 48, or the like. Furthermore, apparatus 30 is not limited to having four reflective surfaces. In alternative embodiments (not shown), apparatus 30 may have one reflective surface, e.g., reflective surface 42, two reflective surfaces, e.g., reflective surfaces 42 and 44 or reflective surfaces 42 and 46, or three reflective surfaces, e.g., reflective surfaces 42, 44, and 46. In these alternative embodiments, the number, location, and orientations of cameras in apparatus 30 are preferably adjusted accordingly.

Figure 4:
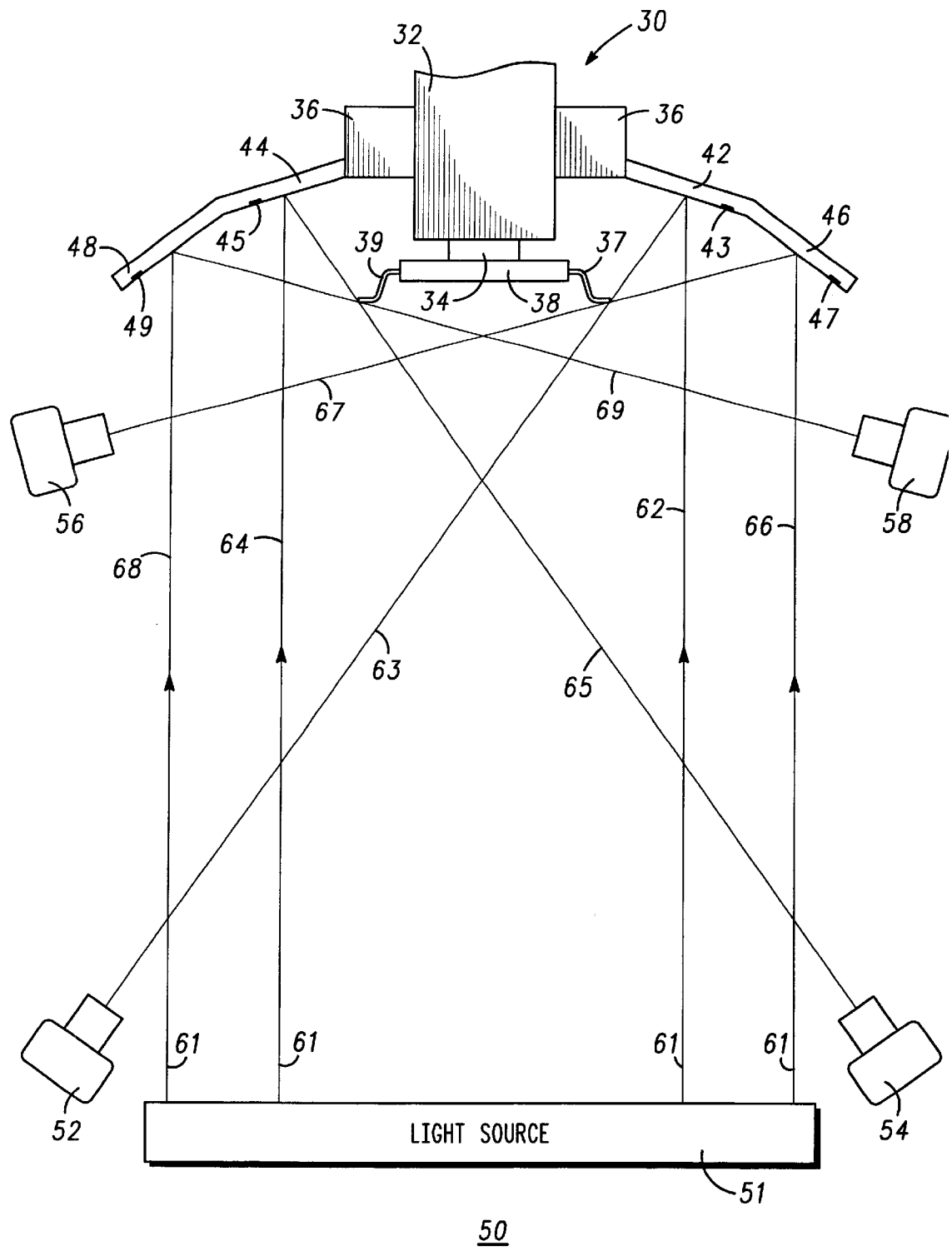
FIG. 4 schematically illustrates a system that uses the apparatus of FIG. 3 for inspecting an object in accordance with the second embodiment of the present invention.

FIG. 4 schematically illustrates a system 50 in accordance with the second embodiment of the present invention. System 50 includes apparatus 30 of FIG. 3 and is used for visually inspecting an object 38. System 50 is also referred to as an optical system or an inspection system. By way of example, object 38 is a semiconductor device has two sets of leads 37 and 39 on the opposite sides thereof. Apparatus 30 picks up semiconductor device 38 from one location and transports it to another location during a semiconductor device packaging process. Inspection system 50 also includes a light source 51 and cameras 52, 54, 56, and 58. Like light source 21 in inspection system 20 of FIG. 2, light source 51 can be a light source, e.g., a light emitting diode, that emits a continuous light, or a strobe light source. Cameras 52, 54, 56, and 58 record the silhouette images of semiconductor device 38 formed by a light beam 61 emitted from light source 51. A vision computer (not shown) coupled to cameras 52, 54, 56, and 58 analyzes the images and examines the geometrical property of semiconductor device 38 and the position and orientation of semiconductor device 38 relative to apparatus 30.

In the visual inspection process, light source 51 emits light beam 61 that illuminates reflective surfaces 42, 44, 46, and 48 of apparatus 30. By way of example, light beam 61 is a substantially collinear light beam substantially parallel to pole 32. A portion 62 of light beam 61 is reflected by reflective surface 42, thereby generating a deflected light beam 63, which back lights set of leads 37 of semiconductor device 38 and forms a silhouette image thereof in camera 52. A portion 66 of light beam 61 is reflected by reflective surface 46, thereby generating a deflected light beam 67, which back lights set of leads 37 of semiconductor device 38 and forms a silhouette image thereof in camera 56. The silhouette images of set of leads 37 formed by deflected light beams 63 and 67 have different directions of views from each other. The image formed by deflected light beam 63 is sometimes referred to as a steep view image of set of leads 37, and the image formed by deflected light beam 67 is sometimes referred to as a shallow view image of set of leads 37. Likewise, a portion 64 and a portion 68 of light beam 61 are reflected by reflective surfaces 44 and 48, respectively, thereby generating deflected respective light beams 65 and 69, which back light set of leads 39 of semiconductor device 38 and form silhouette images thereof in cameras 54 and 58, respectively. The silhouette images of set of leads 39 formed by deflected light beams 65 and 69 have different directions of views from each other. The images formed by deflected light beams 65 and 69 are sometimes referred to as a steep view image and a shallow view image, respectively, of set of leads 39.

A vision computer (not shown) coupled to cameras 52, 54, 56, and 58 analyzes the silhouette images and inspect semiconductor device 38 for parameters such as, for example, lead coplanarity, lead length, lead straightness, mark inspection, surface inspection, lead pitch, etc. If they do not meet a predetermined design specification, semiconductor device 38 is rejected. After the visual inspection, a rejected device is transported to a predetermined location for disposal.

It should be noted that, when apparatus 30 picks up semiconductor device 38, there is usually a variation in the position and orientation of semiconductor device 38 with respect to apparatus 30. This variation will generally result in a variation in the position and orientation of semiconductor device 38 in its final location, which may present a problem in a packaging process that requires a high precision in the final position and orientation of semiconductor device 38. The visual inspection process of the present invention can solve that problem. In accordance with the present invention, the images in cameras 52, 54, 56, and 58 preferably also include the images of reference marks 43, 45, 47, and 49, respectively. Because the geometrical parameters of apparatus 30 such as, for example, the position and orientation of reflective surfaces 42, 44, 46, and 48 with respect to pickup mechanism 34 and the location of reference marks 43, 45, 47, and 49 on respective reflective surfaces 42, 44, 46, and 48 are determined to a high degree of accuracy, analyzing the images provides accurate data about the position and orientation of semiconductor device 38 with respect to apparatus 30. These data are used in adjusting the position and orientation of apparatus 30 when apparatus 30 releases semiconductor device 38, thereby achieving precise position and orientation of semiconductor device 38 in its final location.

It should be understood that the structure and operation of inspection system 50 are not limited to being those described hereinbefore. For example, light source 51 can emit a diffusive light beam. Furthermore, in an alternative embodiment, inspection system 50 includes a group of deflectors (not shown) and cameras 52, 54, 56, and 58 is replaced with a single camera (not shown). The deflectors can be made up of lenses, mirrors, or a combination thereof. The deflectors deflect deflected light beams 63, 65, 67, and 69 after they pass semiconductor device 38 to generate four image beams substantially parallel to each other. Therefore, the four silhouette images of semiconductor device 38 having different directions of views can be formed in the single camera. In another alternative embodiment, inspection system 50 includes two cameras (not shown), the first camera replacing cameras 52 and 56, and the second camera replacing cameras 54 and 58. Deflected light beams 63 and 67 are deflected to form two images beams substantially parallel to each other, thereby forming the steep view image and shallow view image, respectively, of set of leads 37 images in the first camera. Deflected light beams 65 and 69 are deflected to form two images beams substantially parallel to each other, thereby forming the steep view image and shallow view image, respectively, of set of leads 39 in the second camera.

Figure 5:
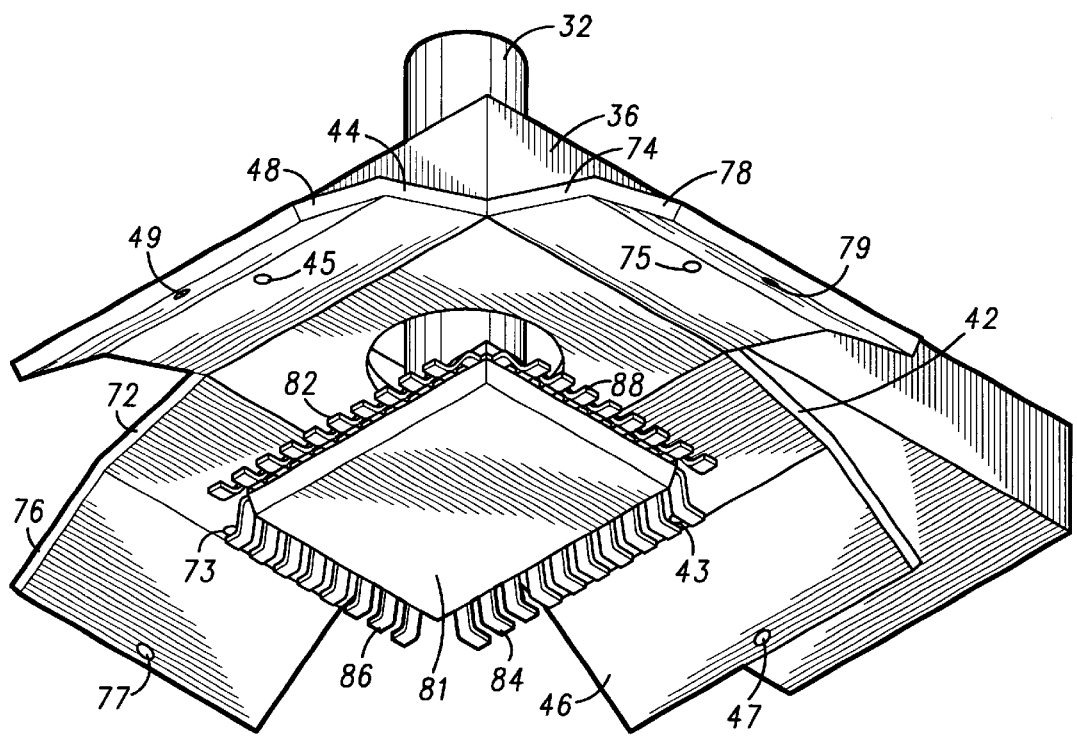
FIG. 5 is an isometric view of an apparatus that can be used for visually inspecting an object in accordance with a third embodiment of the present invention.

FIG. 5 is an isometric view of an inspection apparatus 70 that can be used for visually inspecting an object 81 in accordance with a third embodiment of the present invention. The structure and function of apparatus 70 are similar to those of apparatus 30 of FIG. 3. Apparatus 70 is also referred to as a visual inspection tool or a pickup tool. Like apparatus 30 of FIG. 3, apparatus 70 includes a pole 32, an object pickup mechanism 34, a collar 36, reflective surfaces 42, 44, 46, and 48, and reference marks 43, 45, 47, and 49. In addition, apparatus 70 includes a reflective surface 72 and a reflective surface 74 attached to the opposite sides of collar 36 between reflective surfaces 42 and 44. Each of normal lines (not shown) of reflective surfaces 72 and 74 makes an angle between approximately 5° and approximately 30° relative to a direction parallel to pole 32 (the vertical direction in FIG. 5). A reflective surface 76 and a reflective surface 78 are attached to reflective surfaces 72 and 74, respectively. A normal line (not shown) of reflective surface 76 preferably makes an angle with respect to the direction parallel to pole 32 greater than the normal line of reflective surface 72. Similarly, a normal line (not shown) of reflective surface 78 preferably makes an angle with respect to the direction parallel to pole 32 greater than the normal line of reflective surface 74. By way of example, each of these two angles is between approximately 10° and approximately 45°. Preferably, apparatus 70 includes reference marks 73, 75, 77, and 79 on reflective surfaces 72, 74, 76, and 78, respectively. Like reflective surfaces 42, 44, 46, and 48, reflective surfaces 72, 74, 76, and 78 serve as deflectors and can be polished metal surfaces, mirrors, or the like.

In a preferred embodiment, the four angles between the normal lines of reflective surface 42, 44, 72, and 74 and the direction parallel to pole 32 are substantially equal to each other, and the four angles between the normal lines of reflective surface 46, 48, 76, and 78 and the direction parallel to pole 32 are substantially equal to each other. Preferably, the geometrical parameters of apparatus 70, e.g., the position and orientation of reflective surfaces 42, 44, 46, 48, 72, 74, 76, and 78 with respect to pickup mechanism 34 and the locations of reference marks 43, 45, 47, 49, 73, 75, 77, and 79 on corresponding reflective surfaces 42, 44, 46, 48, 72, 74, 76, and 78 are determined to a high degree of accuracy. Accordingly, the position and orientation of object 81 with respect to apparatus 70 can be accurately measured.

The process of using apparatus 70 to visually inspecting object 81 is similar to that described hereinbefore with reference to FIG. 4. However, apparatus 70 is capable of simultaneously forming eight images of different portions of object 81. By way of example, object 81 is a semiconductor device in a quad flat package, which has sets of leads 82, 84, 86, and 88 on four sides of the package. In a visual inspection process, reflective surfaces 42 and 46 generate two deflected light beams that back light set of leads 82 and form a steep view silhouette image and a shallow view silhouette image, respectively, thereof. Reflective surfaces 44 and 48 generate two deflected light beams that back light set of leads 84 and form a steep view silhouette image and a shallow view silhouette image, respectively, thereof. Reflective surfaces 72 and 76 generate two deflected light beams that back light set of leads 86 and form a steep view silhouette image and a shallow view silhouette image, respectively, thereof. Reflective surfaces 74 and 78 generate two deflected light beams that back light set of leads 88 and form a steep view silhouette image and a shallow view silhouette image, respectively, thereof.

By now it should be appreciated that an apparatus and a method for visually inspecting an object in an automated object handling process have been provided. In accordance with the present invention, the object is picked up by a pickup tool which has embedded optical features. The pickup tool serves as an inspection apparatus. A light source is used to illuminate a portion of the pickup tool adjacent the object when the pickup tool is at a predetermined position relative to the light source. The reflective surfaces attached to the pickup tool reflect portions of the incident light beam emitted from the light source to generate deflected light beams. The light beams back light portions of the object and generate silhouette images thereof. The pickup tool also serves as a reference frame when the images of the object are reconstructed in a vision computer and the geometrical parameters of the object are examined. Therefore, the visual inspection of the object can be performed while the pickup tool picks up the object and moves it from one place to another place. More particularly, the object does not need to be placed on an inspection station for visual inspection. By using the back lighting technique, the present invention provides images generally free of hot spots, cold spots, or other image distortions which are often present in the images formed using the front lighting technique. Because reflective surfaces on the pickup tool serve to provide back light, their optical qualities such as, for example, smoothness and flatness do not need to be as high as those usually required for image forming lenses and mirrors. Therefore, the apparatus of the present is easy to manufacture and cost efficient. The method for performing the visual inspection is simple and time efficient. Further, the inspection process of the present invention is compatible with existing object handling process.

What is claimed is:

1. A visual inspection apparatus, comprising:
   a pole having an end;
   an object pickup mechanism at the end of said pole; and
   a reflective surface coupled to said pole, a normal line of said reflective surface making an angle with respect to a direction substantially parallel to said pole such that a single light source produces a plurality of object silhouettes precisely defining a position and an orientation of the object with respect to the visual inspection apparatus.

2. The visual inspection apparatus of claim 1, wherein said reflective surface makes an angle of approximately 45 degrees with respect to a direction parallel to said pole.

3. The visual inspection apparatus of claim 1, further comprising a shaft surrounding a portion of said pole and having an inclined end surface, on which said reflective surface is formed.

4. The visual inspection apparatus of claim 3, wherein:
   said shaft includes a metal shaft; and
   said reflective surface includes a polished metal surface.

5. The visual inspection apparatus of claim 3, wherein said reflective surface includes a mirror attached to the inclined end surface of said shaft.

6. A visual inspection apparatus, comprising:
   a pole;
   a shaft surrounding a portion of said pole and having an inclined end surface; and
   a mirror formed on said inclined end surface of said shaft; a normal line of said mirror making an angle of with respect to a direction substantially parallel to said pole such that a single light source produces a plurality of object silhouettes precisely defining a postion and an orientation of the object with respect to the visual inspection apparatus.

7. The visual inspection apparatus of claim 6, wherein said normal line of said mirror makes an angle between approximately 5 degrees and approximately 30 degrees with respect to said direction substantially parallel to said pole.

8. The visual inspection apparatus of claim 6, wherein said normal line of said mirror makes an angle of approximately 45 degrees with respect to said direction substantially parallel to said pole.

* * * * *

UNITED STATES PATENT AND TRADEMARK OFFICE
CERTIFICATE OF CORRECTION

PATENT NO.    : 6,404,912 B1
DATED         : June 11, 2002
INVENTOR(S)   : David Charles Lehnen et al.

It is certified that error appears in the above-identified patent and that said Letters Patent is hereby corrected as shown below:

<u>Column 10,</u>
Line 14, delete the second occurrence of "of".

Signed and Sealed this

Thirtieth Day of December, 2003

JAMES E. ROGAN
*Director of the United States Patent and Trademark Office*